(12) United States Patent
Voorhees et al.

(10) Patent No.: US 10,588,779 B2
(45) Date of Patent: *Mar. 17, 2020

(54) PATIENT TEMPERATURE RESPONSE CONTROL SYSTEM AND METHOD

(71) Applicant: Medivance Incorporated, Louisville, CO (US)

(72) Inventors: Marc Voorhees, Arvada, CO (US); Gary A. Carson, Golden, CO (US); Gary Gruszecki, Golden, CO (US)

(73) Assignee: Medivance Incorporated, Louisville, CO (US)

( * ) Notice: Subject to any disclaimer, the term of this patent is extended or adjusted under 35 U.S.C. 154(b) by 318 days.

This patent is subject to a terminal disclaimer.

(21) Appl. No.: 15/683,546

(22) Filed: Aug. 22, 2017

(65) Prior Publication Data

US 2017/0348145 A1 Dec. 7, 2017

Related U.S. Application Data

(63) Continuation of application No. 14/864,532, filed on Sep. 24, 2015, now Pat. No. 9,763,823, which is a
(Continued)

(51) Int. Cl.
*A61B 5/00* (2006.01)
*A61F 7/00* (2006.01)
(Continued)

(52) U.S. Cl.
CPC .............. *A61F 7/0097* (2013.01); *A61B 5/01* (2013.01); *A61B 5/11* (2013.01); *A61B 5/1101* (2013.01);
(Continued)

(58) Field of Classification Search
CPC .............. A61B 5/01; A61B 2010/0019; A61B 2560/0209; A61B 2560/0412; A61B 5/6833; A61B 5/1123; A61B 5/4094
(Continued)

(56) References Cited

U.S. PATENT DOCUMENTS 5,195,531 A * 3/1993 Bennett ..................... A61B 5/03
600/546
5,862,803 A * 1/1999 Besson .............. A61B 5/14552
128/903

(Continued)

FOREIGN PATENT DOCUMENTS

| EP | 0846440 A2 | 6/1998 |
| WO | 1996036950 A1 | 11/1996 |
| WO | 2007121480 A3 | 10/2007 |

OTHER PUBLICATIONS

Michael Sung, et al., Shiver Motion and Core Body Temperature Classification for Wearable Soldier Health Monitoring Systems, MIT Media Laboratory, Human Dynamics Group, 4 Pages Oct. 31, 2004.

*Primary Examiner* — May A Abouelela
(74) *Attorney, Agent, or Firm* — Rutan & Tucker LLP

(57) ABSTRACT

A system and method are provided that employ a monitoring device to monitor at least one patient physiological response to a change in temperature of the patient (e.g. pursuant to induced hypothermia therapy), wherein a monitoring signal is provided by the monitoring device. In turn, an output (e.g. a visual and/or auditory output) may be provided to a user indicative of at least one measure of patient response to the change in temperature. Alternatively or additionally, a processor may be provided to process the monitoring signal and provide an output employable by medical personnel to control a patient shivering response to the patient temperature change. Such information may comprise information
(Continued)

regarding one or more anti-shivering medicament(s), e.g. corresponding dosage and/or frequency information for use by medical personnel in the administration of the anti-shivering medicament. In one approach, a motion sensor may be selectively attached to a patient's chin to provide a wireless monitoring signal to a transceiver. In turn, the transceiver may provide the monitoring signal to the processor on an ongoing basis to output information useful in the administration of an anti-shivering medicament, including updated information that takes into account a patient's response to a prior administration of one or more medicaments in conjunction with the subsequent administration of an anti-shivering medicament.

15 Claims, 14 Drawing Sheets

Related U.S. Application Data continuation of application No. 12/272,643, filed on Nov. 17, 2008, now abandoned.

(60) Provisional application No. 60/988,706, filed on Nov. 16, 2007.

(51) Int. Cl.
*A61B 5/01* (2006.01)
*A61B 5/11* (2006.01)
*A61F 7/02* (2006.01)
*A61B 5/026* (2006.01)
*A61B 5/0488* (2006.01)
*A61B 5/083* (2006.01)
*A61B 5/1455* (2006.01)
*A61B 34/00* (2016.01)

(52) U.S. Cl.
CPC .......... *A61B 5/4035* (2013.01); *A61B 5/6814* (2013.01); *A61B 5/6828* (2013.01); *A61B 5/68335* (2017.08); *A61B 5/7435* (2013.01); *A61F 7/02* (2013.01); *A61B 5/026* (2013.01); *A61B 5/0488* (2013.01); *A61B 5/0836* (2013.01); *A61B 5/1455* (2013.01); *A61B 5/6824* (2013.01); *A61B 34/25* (2016.02); *A61B 2562/0219* (2013.01); *A61F 2007/0056* (2013.01); *A61F 2007/0093* (2013.01)

(58) Field of Classification Search
USPC .......... 600/300, 301, 587, 595; 340/575; 607/96, 104
See application file for complete search history.

(56) References Cited

U.S. PATENT DOCUMENTS

| | | | |
|---|---|---|---|
| 6,141,572 A | 10/2000 | Haas | |
| 6,149,670 A | 11/2000 | Worthen et al. | |
| 6,188,930 B1* | 2/2001 | Carson | A61N 5/045 128/898 |
| 6,197,045 B1 | 3/2001 | Carson | |
| 6,198,394 B1* | 3/2001 | Jacobsen | A61B 5/1112 340/573.1 |
| 6,231,594 B1* | 5/2001 | Dae | A61F 7/123 607/106 |
| 6,238,354 B1 | 5/2001 | Alvarez | |
| 6,290,717 B1 | 9/2001 | Philips | |
| 6,375,674 B1 | 4/2002 | Carson | |
| 6,432,124 B1 | 8/2002 | Worthen et al. | |
| 6,454,793 B1 | 9/2002 | Evans et al. | |
| 6,461,379 B1 | 10/2002 | Carson et al. | |
| 6,582,457 B2 | 6/2003 | Dae et al. | |
| 6,620,187 B2* | 9/2003 | Carson | A61F 7/0085 607/104 |
| 6,645,232 B2 | 11/2003 | Carson | |
| 6,648,905 B2 | 11/2003 | Hoglund et al. | |
| 6,660,027 B2 | 12/2003 | Gruszecki et al. | |
| 6,669,715 B2 | 12/2003 | Hoglund et al. | |
| 6,682,551 B1 | 1/2004 | Worthen et al. | |
| 6,692,518 B2 | 2/2004 | Carson | |
| 6,699,267 B2 | 3/2004 | Voorhees et al. | |
| 6,702,839 B1 | 3/2004 | Dae et al. | |
| 6,726,710 B2 | 4/2004 | Worthen et al. | |
| 6,799,063 B2 | 9/2004 | Carson | |
| 6,802,855 B2 | 10/2004 | Ellingboe et al. | |
| 6,818,012 B2 | 11/2004 | Ellingboe | |
| 6,827,728 B2 | 12/2004 | Ellingboe et al. | |
| 6,921,198 B2 | 7/2005 | Gruszecki et al. | |
| 7,008,444 B2 | 3/2006 | Dae et al. | |
| 7,294,112 B1* | 11/2007 | Dunlop | A61B 5/1118 600/534 |
| 7,361,186 B2 | 4/2008 | Voorhees et al. | |
| 7,827,815 B2 | 11/2010 | Carson et al. | |
| 8,047,010 B2 | 11/2011 | Carson et al. | |
| 8,663,106 B2* | 3/2014 | Stivoric | G06F 19/3418 600/301 |
| 2002/0091308 A1 | 7/2002 | Kipshidze et al. | |
| 2002/0165590 A1* | 11/2002 | Crowe | A61N 1/36003 607/48 |
| 2003/0092975 A1* | 5/2003 | Casscells, III | A61B 5/01 600/300 |
| 2003/0163183 A1 | 8/2003 | Carson | |
| 2004/0064169 A1 | 4/2004 | Briscoe et al. | |
| 2004/0073280 A1 | 4/2004 | Dae et al. | |
| 2004/0087606 A1* | 5/2004 | Voorhees | A61K 31/403 514/282 |
| 2004/0143170 A1 | 7/2004 | DuRousseau | |
| 2004/0210166 A1 | 10/2004 | Soh et al. | |
| 2005/0065583 A1* | 3/2005 | Voorhees | A61F 7/10 607/104 |
| 2006/0190062 A1* | 8/2006 | Worthen | A61F 7/10 607/96 |
| 2007/0063850 A1 | 3/2007 | Devaul et al. | |
| 2007/0118054 A1* | 5/2007 | Pinhas | A61B 5/1104 600/587 |
| 2007/0129622 A1* | 6/2007 | Bourget | A61B 5/0002 600/382 |
| 2007/0173705 A1* | 7/2007 | Teller | A61B 5/02055 600/300 |
| 2007/0191918 A1* | 8/2007 | MacHold | A61M 25/10 607/105 |
| 2008/0071150 A1* | 3/2008 | Miesel | A61B 5/1116 600/301 |
| 2008/0167535 A1* | 7/2008 | Stivoric | F24F 11/30 600/301 |
| 2009/0033333 A1* | 2/2009 | Gribova | A61B 5/04 324/439 |
| 2009/0099629 A1 | 4/2009 | Carson et al. | |
| 2009/0131835 A1 | 5/2009 | Voorhees et al. | |
| 2009/0149779 A1* | 6/2009 | Russo | A61B 5/02405 600/595 |
| 2010/0087900 A1 | 4/2010 | Flint | |

* cited by examiner

SVD (SINGLE VALUE DECOMPOSITION)
SPATIAL ANALYSIS $$W_{avg} = U \cdot \Sigma \cdot V^T$$

ELLIPTICAL PARAMETERS ANALYSIS AXES
(AKA SINGULAR VALUES)

THE SMALLEST ELLIPTICAL PARAMETER, $\sigma_{min}$, CORRESPONDS TO THE AXIS OF MOST CONSTRAINED MOTION CONDITION RATIO = $\sigma_{max}/\sigma_{min}$ MINOR AXIS OF MOTION = $V_{min}$ WHERE $V_{min}$ IS THE COLUMN VECTOR OF V THAT CORRESPONDS TO $\sigma_{min}$ $|v_{min}(i) \cdot v_{min}(i-1)|$ YIELDS A VALUE BETWEEN 0 AND 1 THAT REPRESENTS THE PERSISTENCE OF THE PLANE OF MOTION FROM BLOCK TO BLOCK

FIG. 9C

PATIENT TEMPERATURE RESPONSE CONTROL SYSTEM AND METHOD

RELATED APPLICATIONS

This application is a continuation of U.S. patent application Ser. No. 14/864,532, filed Sep. 24, 2015, entitled "PATIENT TEMPERATURE RESPONSE CONTROL SYSTEM AND METHOD", now U.S. Pat. No. 9,763,823, which is a continuation of U.S. patent application Ser. No. 12/272,643, filed Nov. 17, 2008, entitled "PATIENT TEMPERATURE RESPONSE CONTROL SYSTEM AND METHOD", which claims benefit of priority to U.S. Patent Provisional Application Ser. No. 60/988,706, filed Nov. 16, 2007, entitled "PATIENT TEMPERATURE RESPONSE CONTROL SYSTEM AND METHOD", all of which applications are incorporated herein by reference in their entirety.

FIELD OF THE INVENTION

The present invention relates to the field of induced hypothermia, and in particular, to a system and method that facilitates the control of patient shivering discomfort associated with induced hypothermia therapy.

BACKGROUND OF THE INVENTION

Hypothermia is a condition in which body temperature is at a level lower than normal body temperature. Therapeutic induced mild-moderate hypothermia can be beneficial for people suffering stroke, myocardial infarction, cardiac arrest serious head trauma and other conditions involving reduced blood supply. One method for lowering body temperature is to insert a cooling device into an artery of the patient and to internally cool the patient's body by introducing a cooling fluid into the device. A non-invasive technique for lowering body temperature is to externally cool the exterior surface of the patient's body. Such exterior surface cooling could be achieved, for example, by direct contact with a cooling fluid, such as by immersing the patient's body in the cooling fluid or by directing the flow of the cooling fluid around the patient's body. The cooling fluid could be, for example, cool water or cool air. Another technique for external surface cooling is to apply a contact-cooling pad to the exterior surface of the patient and to circulate a cooling fluid, such as water or an aqueous solution, through the contact pad to cool the patient.

For therapeutic purposes, it is often desirable for the mild-moderate hypothermia to be induced very quickly. With endovascular cooling, heat is removed directly from blood flowing through blood vessels. Blood with reduced temperature moves through blood vessels to cool other parts of the body. With exterior surface cooling, heat is removed across the patient's skin. Cooling of the skin increases conduction of heat from deeper within the body, thereby cooling internal body tissue. Blood moving through blood vessels in a cooled portion of the body is also cooled, and distribution of that cooled blood to other parts of the body thereby contributes to cooling other parts of the body.

Quick inducement of hypothermia requires that the patient's body temperature be rapidly reduced to the desired level, and involves a high rate of transfer of heat from the body. Impediments to inducing hypothermia include the patient's thermoregulatory responses to cooling. Shivering is a common thermoregulatory response that, in some cases, can increase body heat production to as much as 600% above basal levels. Anti-shivering drugs, and particularly meperidine, have been administered prior to or during active cooling to help suppress the shivering response. Such pharmacological treatment to suppress shivering is often successful, resulting in more rapid lowering of the patient's body temperature to more quickly induce a desired degree of hypothermia, reducing patient tiring attendant to shivering, and also reducing patient discomfort associated with shivering.

SUMMARY OF THE INVENTION

In view of the foregoing, one objective of the present invention is to facilitate control over, and thereby reduce, patient shivering (e.g. in response to induced hypothermia).

A related objective of the present invention is to facilitate a reduction in patient shivering, and attendant patient heat production, patient tiring and patient discomfort(e.g. in induced hypothermia procedures) via a system and method that provide an output to facilitate anti-shivering response by medical personnel and that otherwise exhibit user-friendly functionalities.

Yet another objective is to facilitate a reduction in patient shivering (e.g. during induced hypothermia procedures) in a manner that enhances the efficiency of medical personnel in the performance of thermotherapy related activities.

One or more of the above objectives and additional advantages may be realized in a medical apparatus that includes a monitoring device for monitoring patient shivering or at least one physiological response of a patient to a change in the temperature of the patient and to provide a monitoring signal responsive thereto. The inventive apparatus may further include an output device for providing an output to a user responsive to the monitoring signal. In this regard, the output may be indicative of at least one measure of a physiological response, such as a magnitude, degree or progressive stage of shivering and/or information regarding potential response treatment option(s). By way of example, a visual and/or auditory output may be provided to a user that indicates that a predetermined level or stage of shivering has been detected and/or other information that may be useful in addressing a detected patient shivering condition.

In one aspect, the medical apparatus may further comprise at least one of an energy storage device and a wireless energy conversion device, interconnected to the monitoring device, for powering the monitoring device. In one approach, a wireless signal receiver and rectifier arrangement may be employed for receiving a wireless signal and transducing electrical energy therefrom to power the monitoring device. In conjunction with such approach, a wireless signal transmitter may be employed for transmitting a wireless signal corresponding with the monitoring signal. Alternatively, a transceiver may be employed for both receiving a wireless signal and transmitting a wireless signal corresponding with the monitoring signal.

In another approach, a battery may be employed as an energy storage device for powering the monitoring device. In conjunction with such approach, the battery may be interconnected with a transmitter for transmission of a wireless signal corresponding with the monitoring signal. Further, when a rechargeable battery is employed, a wireless signal receiver and rectifier may be included to transduce electrical energy from a wireless charging signal for recharging the rechargeable battery.

In conjunction with either of the above-noted approaches, an energy storage device and/or wireless energy conversion device may be interconnected to a monitoring device for co-movement therewith. More particularly, such components may be directly connected or interconnected to a common support member for co-movement, free from hardwire or other physical interconnections with a power source.

In a related aspect, the monitoring device may be non-invasive. In turn, use of the monitoring device may be initiated without compounding patient anxiety, patient tiring or patient discomfort otherwise attendant to the use of invasive devices.

In a further related aspect, the monitoring device may be provided to be selectively interconnectable to and disconnectable from a patient. When connected, the monitoring device may be maintainable in fixed relation to a given location on a patient. By way of example, the monitoring device may be interconnectable to a patient via a hook and loop fastener arrangement, a peel and stick adhesive surface arrangement or other like techniques.

In one approach, the monitoring device may comprise at least one motion sensor, e.g. an accelerometer selectively interconnectable/disconnectable to a patient, e.g. adhesively connectable to a patient's jaw (e.g. the masseter region). Such accelerometer(s) may be provided to measure acceleration in one and/or a plurality of orthogonal axes (e.g. one, two or three orthogonal axes).

In conjunction with such approach, a plurality of accelerometers may be interconnected to a patient at different locations to provide separate monitoring signals that may be employed together to facilitate the provision of an output indicative of a magnitude, degree or stage of patient shivering. For example, accelerometers may be separately interconnected to a patient's jaw (e.g. the masseter region), to a patient's chest (e.g. the pectoral region), to a patient's arm (e.g. the bicep region) and/or to a patient's leg (e.g. the quadriceps region), wherein corresponding monitoring signals from such accelerometers may be utilized to monitor a degree and for progressive stage of shivering. In this regard, each of the monitoring signals may comprise pre-determined signal portions (e.g. corresponding with a predetermined motion frequency range or ranges) whose presence and/or magnitude may be identified and utilized to generate a user output.

In another approach, the monitoring device may comprise a vasoconstriction measurement device for measuring blood flow at two to offset locations, e.g. at a fingertip and at corresponding forearm. In an additional approach, the monitoring device may comprise one or more electromyography (EMG) surface sensors for monitoring muscular electrical activity. In another approach, the monitoring device may comprise a pulse oximeter sensor for monitoring blood oxygen saturation levels of a patient. In yet a further approach, the monitoring device may comprise one or more capnography input sensors for concentration and/or partial pressure of carbon dioxide in patient respiratory gases.

In relation to each of these approaches, the monitored parameter may have a known relationship to patient shivering, wherein a magnitude of the measured parameter may be related to a corresponding degree or stage of patient shivering. Further, in relation to such approaches, a plurality of sensors that measure the same parameter and/or different ones of the noted parameters may be employed to combinatively yield a monitoring signal.

In certain embodiments, a processor and/or logic circuit may be employed to process one or more monitoring signal(s) to generate an output control signal for controlling an output device. In this regard, one or more predetermined algorithms may be employed for frequency domain processing and/or time domain processing of one or a plurality of monitoring signal(s) provided by one or a plurality of motion monitoring device(s) (e.g. one or a plurality of accelerometer(s)).

In one approach, a monitoring signal comprising three-dimensional accelerometer output data values may be processed utilizing a frequency domain transfer algorithm. In this regard, successive overlapping frames of data sets which each comprise three dimensional acceleration data values may be deinterleaved into three data sets corresponding with each of the three dimensions, windowed (e.g. utilizing a Kaiser or other windowing technique) and transformed utilizing a frequency transform technique (e.g. a Fourier transform). A square of the modulus of the transformed data may be determined, and the results thereof may be summed to yield spectral data for each frame of data. In turn, the spectral data for a plurality of frames may be analyzed in relation to a plurality of predetermined frequency ranges to assess a magnitude or degree of patient shivering, wherein at least one of the predetermined frequency bands includes a frequency level indicative of patient shivering (e.g. a band including a frequency level of about 9.5 Hz).

In another aspect, the processor may be pre-programmed to process the monitoring signal and provide information for use in administering at least one anti-shivering medicament to a patient. By way of example, such information may comprise the identification of one or more anti-shivering medicaments employable by medical personnel in controlling patient shivering. Further, the output may comprise information corresponding with dosage and/or administration frequency of one or more anti-shivering medicaments. In one approach, dosage and frequency information may be based upon, at least in part, a monitored magnitude of patient shivering, as reflected by the monitoring signal.

The anti-shivering medicament may comprise one or more substance effective for suppressing shivering. A variety of such anti-shivering medicaments are known or may be identified in the future. Examples of some reported anti-shivering medicaments include certain non-opioid analgesics (e.g. tramodol and nefopan), certain opioid analgesics (e.g. alfentanil, morphine, fentanyl, meperidine, naloxone and nalbuphine), certain $\alpha_2$-andrenergic agonists (e.g. clonidine and dexmedetomidine) and certain serotonin antagonists (e.g. ketanserin and ondansetron). Also, multiple anti-shivering medicaments may be used to the extent they are pharmacologically compatible. Moreover, it should be appreciated that medicaments are often administered in the form of pharmacologically acceptable salts, so, for example, the anti-shivering medicament may be such a salt of any of the foregoing listed compounds. Meperidine, or a salt thereof, is particularly preferred for use as the anti-shivering drug.

Given the variety of anti-shivering medicaments that may be employable, and in another aspect, the processor may be preprogrammed to generate information, at least in part, in accordance with a user-established protocol that specifies one or more user-preferred anti-shivering medicaments and that comprises data and/or algorithms that provide for the automated generation of an output regarding dosage and/or frequency information for the preferred medicament(s). For example, a given user may pre-establish a protocol that contemplates the use of a particular medicament and a corresponding dosage amount and/or frequency of dosage administration rate, as well as a preset correlation between such data and measured magnitude(s) of monitored patient response to temperature change (e.g. a monitored magnitude of patient shivering).

In an additional aspect, the processor may be operable to process the monitoring signal to assess a given patient's shivering response to at least one prior administration of an anti-shivering medicament, and in turn, to provide output comprising updated information employable in a subsequent administration of the same or different anti-shivering medicament. Stated differently, the processor may process the monitoring signal on an ongoing basis so as to establish trend data corresponding with a patient's response to a given anti-shivering medicament, and in turn, to utilize such trend data in the provision of further updated information regarding a recommended dosage in/or frequency for one or more subsequent administration(s) of an anti-shivering medicament.

In another aspect, the apparatus may include a user interface as an output device for providing output information in at least one of an audible and visual form. By way of example, the information may be provided via an interactive display. In turn, the interactive display may be provided to receive user input, e.g. to identify an anti-shivering medicament and/or to establish a protocol for subsequent use in generating an information output in a given thermotherapy procedure.

As noted above, the monitoring device(s) may be adapted to provide the monitoring signal(s) as a wireless signal(s). In turn, the apparatus may include a receiver, interconnected to a processor, for receiving a wireless monitoring signal and providing the signal to the processor. In turn, the process may process the monitoring signal(s) as indicated above.

In yet another aspect, the processor may be operable to employ the monitoring signal in conjunction with the generation of an input signal that is provided to a temperature control system (e.g. a system for cooling and/or warming a patient). For example, the input signal may be utilized in conjunction with establishing the temperature of a cooling medium utilized to cool a patient.

An inventive method is also provided for use in controlling a shivering response of a patient during therapeutic patient cooling. The method may comprise the steps of monitoring at least one physiological response of a patient to a change in temperature of the patient, and automatically providing an output responsive to the monitoring signal.

In one approach, the output may be indicative of at least one measure of the patient shivering response. For example, the output may comprise a visual and/or audible output indicating to a user a predetermined magnitude, degree and/or stage of patient shivering. In another approach, the output may be based at least in part on a monitored response for employment by a user in controlling the patient's shivering response to a temperature change. For example, the output may comprise information regarding the dosage and/or frequency of administration of an anti-shivering medicament.

In one aspect, the method may further include the step of powering the monitoring device by at least one of an energy storage device and a wireless energy conversion device (e.g. comprising a receiver antenna and rectifier) interconnected to the monitoring device for co-movement therewith. By way of example, the monitoring device (e.g. a motion sensor) and an energy storage device and/or a wireless energy conversion device may each be interconnected to a common support structure (e.g. a printed circuit board located within a protective housing), wherein an adhesive backing may be provided on the support structure with a removable liner to facilitate selective interconnection to and disconnection from a patient.

In a further aspect, the method may include the steps of transmitting the monitoring signal as a wireless signal, and receiving the wireless monitoring signal for use in the providing step. Further, the powering step may include converting a wireless power signal to an electrical signal utilizing a wireless energy conversion device, wherein the electrical signal provides power to the monitoring device for use in the monitoring step and to a transmitter for use in the transmitting step.

In a further aspect, the monitoring step may include utilizing a motion sensor interconnected to a patient to provide a monitoring signal that is indicative of patient motion. In turn, the providing step may include processing of motion data comprising the monitoring signal utilizing frequency domain processing. By way of example, the motion data may include three-dimensional accelerometer data. The processing step may include the steps of windowing the three-dimensional motion data, and transforming the windowed three-dimensional motion data to frequency domain data. In turn, a statistical analysis may be performed on the frequency domain data in a relation to a plurality of predetermined frequency bands.

In yet another aspect, the monitoring step may comprise at least one of monitoring motion of the patient (e.g. shivering-related motion), monitoring vasoconstriction of the patient (e.g. based on relative blood flow measurements at offset vascular locations), monitoring muscular electrical activity of the patient (e.g. using EMG surface sensors), monitoring carbon dioxide concentration and/or partial pressure of respiratory gases of the patient, and/or monitoring blood oxygen saturation levels of the patient. By way of example, a motion sensor may be selectively interconnected to a patient to monitor a magnitude of patient shivering and to provide a monitoring signal reflective thereof. In turn, the generating step may entail a comparison of the monitored shivering magnitude value to one or more preset, reference values. For example, a comparison may yield an indication of moderate shivering magnitude, which in turn may yield an output that indicates that administration of a moderate dosage of a given anti-shivering medicament may be in order.

In another aspect, the method may include the step of administering at least one anti-shivering medicament. For example, the medicament may be administered in accordance with output information that comprises dosage and/or frequency information for one or more identified anti-shivering medicaments.

In a related aspect, following administration of an anti-shivering medicament, the method may provide for repeating the monitoring and processing steps a plurality of times, on an ongoing basis during induced thermo therapy, and utilizing data inputted by a user that corresponds with the prior administering step (e.g. the time and dosage of administration) in a subsequently performed processing step to provide updated output information employable in a subsequent administering step. Stated differently, after the administration of a given anti-shivering medicament, the monitoring and processing steps may establish trend data regarding a patient's response to the anti-shivering medicament. In turn, such trend data may be utilized in the further generation of an output reflecting dosage and/or frequency information for the further administration of an anti-shivering medicament.

In another aspect, the generating step of the inventive method may comprise utilizing patient specific data provided by a user. For example, a user may input data regarding a patient's age, weight, sex, physical condition and/or other patient specific data that may impact the type, amount and/or frequency of medicament administration.

In a further related aspect, the method may provide for outputting information to a user in at least one of a visual form and an audible form. Relatedly, an interactive user interface may be provided for receiving input from a user for use in completing the generating step.

Additional aspects and advantages in the present invention will be apparent to those skilled in the art upon consideration of the further description that follows.

BRIEF DESCRIPTION OF THE DRAWINGS

FIGS. 9A, 9B and 9C illustrates steps of a time domain processing embodiment for processing a monitoring signal in one embodiment of the present invention.

DETAILED DESCRIPTION

Figure 1:
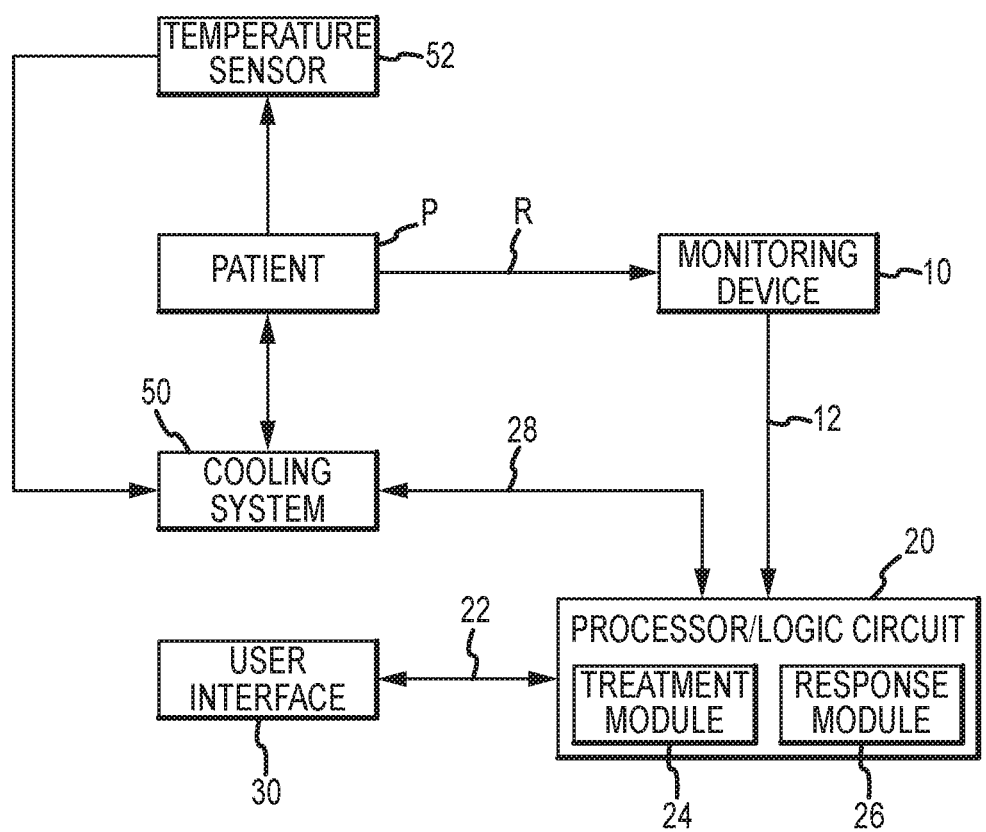
FIG. 1 is a schematic illustration of one apparatus embodiment of the present invention.

FIG. 1 illustrates one embodiment of the present invention. As shown, a monitoring device 10 is provided to monitor at least one physiological response R of a patient P to a change of temperature of the patient and to provide a monitoring signal 12 responsive thereto. By way of example, therapeutic hypothermia may be induced by a cooling system 50. Cooling system 50 may comprise any of a number of different modalities for selective cooling of a patient, including for example cooled contact pads, vascular cooling, patient emersion approaches and/or other systems for rapidly cooling a patient, e.g. systems as described in U.S. Pat. Nos. 6,669,715, 6,827,728, 6,375,674, and 6,645,232, and in WO/2007/121480, hereby incorporated by reference in their entirety.

With further reference to FIG. 1, the monitoring signal 12 may be provided to a processor and/or logic circuit 20 via a hardwire and/or wireless interface between monitoring device 10 and processor and/or logic circuit 20. In turn, processor and/or logic circuit 20 may be preprogrammed or otherwise provided to utilize the monitoring signal 12 to provide an output 22.

In one approach, processor and/or logic circuit 20 may be provided to assess the monitoring signal 12 and provide an output 22 employable to indicate at least one measure of a shivering response of a patient. For example, the output 22 may be employable to provide a visual and/or audible output at a user interface 30 or other output device (e.g. one or more lights (e.g. one or more light emitting diodes) co-located with the patient P), wherein such output provide a user with an indication of a magnitude, degree and/or stage of a patient shivering response to a cooling therapy.

In another approach, an output 22 may be provided that is employable for use in controlling a shivering response of the patient P to changes of the bodily temperature of the patient P. In one embodiment, an output 22 may be provided at user interface 30 which comprises information that corresponds with one or more approaches for controlling patient shivering response via the administration of one or more anti-shivering medicaments.

By way of example, processor 20 may comprise preprogrammed logic, or algorithms/data, in a treatment module 24 for processing the monitoring signal 12 to provide an output 22 comprising information relating to one or more anti-shivering medicament administration actions that may be followed by medical personnel to treat patient shivering response to bodily cooling. In this regard, the treatment module 24 may comprise stored data/algorithms in relation to a plurality of preset treatment protocols, including protocols that have been established by a user, e.g. via user input at interface 30. For example, each pre-established protocol may include data/algorithms relating to one or more of the following:

Data corresponding with different anti-shivering medicament option(s), including different types and/or combinations of anti-shivering medicaments; and Dosage/frequency data and/or algorithms for each anti-shivering medicament option.

As may be appreciated, the processor 20 and the user interface 30 may be provided for interactive operations therebetween. More particularly, in conjunction with a given patient cooling procedure, a user may utilize user interface 30 to access and select a given one of a plurality of treatment protocols, e.g. corresponding with a given protocol established at a given user site (e.g. for a particular physician). In turn, such protocol may provide for the selection of a given one of a plurality of different anti-shivering medicament options (e.g. via an interactive menu).

In turn, for a selected option, the processor 20 may be operative to provide treatment-dosage (e.g. amount) and frequency-of-dosage information to a user at user interface 30. Such information may be provided so as to take into account specific data inputted by a user at a user interface 30 for a given procedure, including for example, patient-specific information (e.g. age, weight, sex etc.), and patient procedure-specific information (e.g. thermotherapy pursuant to stroke, thermotherapy pursuant to head trauma, etc.). Additionally and/or alternatively, the information comprising the output 22 may be based, at least in part, upon a magnitude of the measured patient response R reflected by monitoring signal 12. For example, a magnitude measure may be obtained from the signal 12 and compared with pre-established reference data to assess how much and/or how often a given anti-shivering medicament may be appropriate for administration.

As illustrated in FIG. 1, processor 20 may further comprise a response module 26 comprising algorithms and/or data for processing the monitoring signal 12 on an ongoing basis, e.g. after initiation of patient shivering response actions by a user (e.g. administration of an anti-shivering medicament), to assess the effectiveness of such actions, wherein such assessment may then be automatically employed in the generation of subsequent output 22. To yield such functionality, user interface 30 may be employable to receive user input regarding the patient shivering response actions taken by a user, e.g. the identification of the type(s), dosage amount(s) and time(s) of administration of one or more anti-shivering medicament(s). Such input may be store and/or otherwise employed by response module 26 in completing the above-noted assessment. By way of example, the above-noted assessments may include an algorithmic assessment as to the degree of patient shivering reduction and/or the duration of shivering reduction and/or the degree of shivering reduction on a time-scale basis associated with a given anti-shivering medicament administration procedure (e.g. collectively "trend data"). In turn, the response module 26 may be provided to interface with treatment module 24 to provide information in output 22 regarding potential further treatment action on an ongoing basis during a given patient cooling procedure. Such ongoing treatment information may be provided to a user through user interface 30, wherein such further information is based in part on the trend data assessment.

In addition to the above-described functionalities, the processor 20 may be further adapted for providing an input signal 28 to the cooling system 50. Such input signal 28 may employ with a patient temperature sensor 52 output signal 54 to establish a degree of cooling and/or rate of cooling of the given patient P. For example, based upon a measured magnitude of patient response R, a cooling rate may be increased (e.g. when no shivering is detected and more rapid cooling is therapeutically desired) or decreased (e.g. when an undesirably high degree of shivering is detected and therapeutic rapid cooling is realizable at a lower cooling rate).

Figure 2:
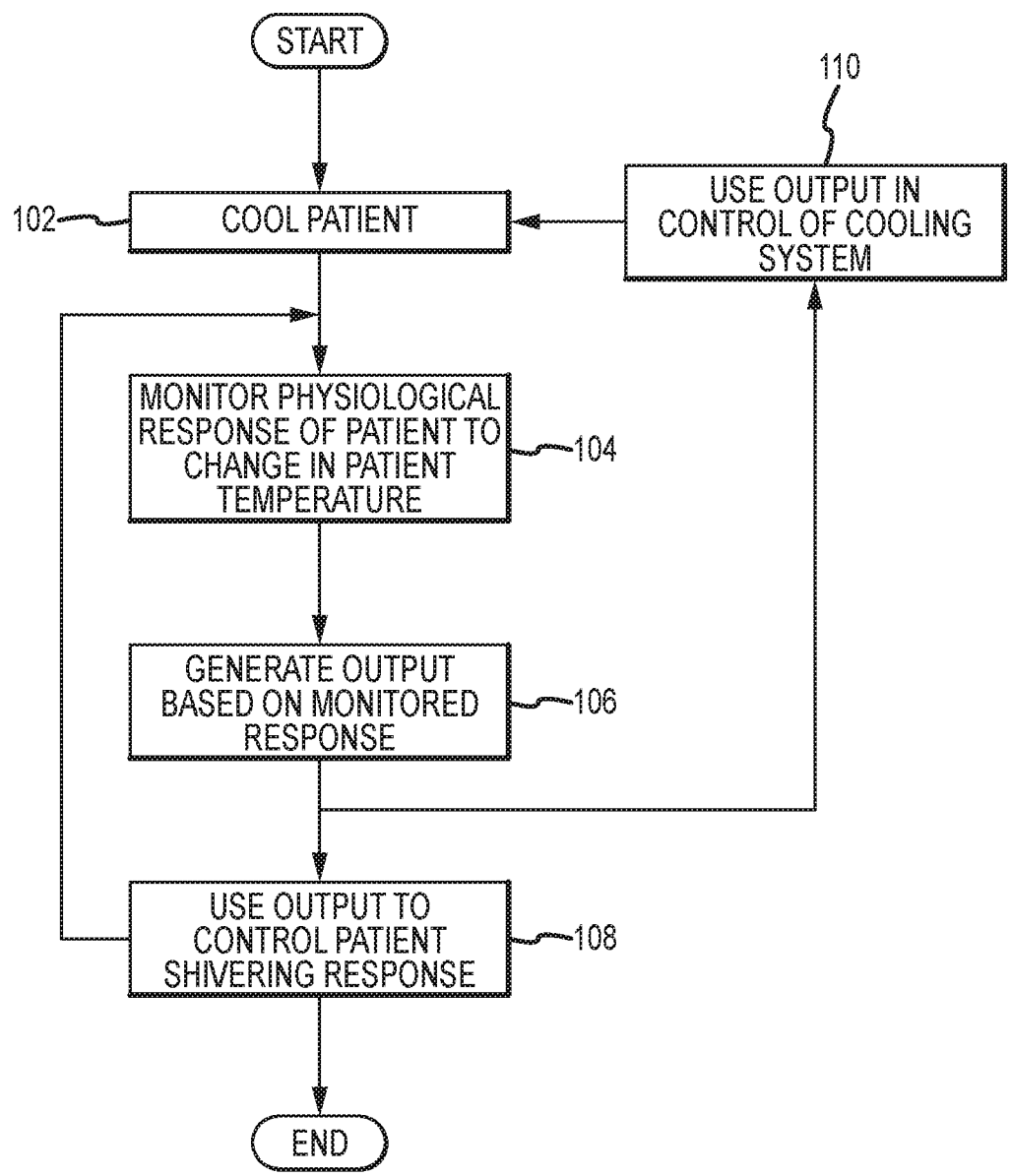
FIG. 2 is a process flow diagram of one method embodiment of the present invention.

Reference is now made to FIG. 2, which illustrates one embodiment of a method comprising the present invention. Initially, pursuant to a given patient treatment condition, e.g. a stroke, serious head trauma or other like event, a patient cooling procedure may be initiated, pursuant to which a patient is as rapidly cooled to reduce risk of neurological damage, step 102. In conjunction with the patient cooling procedure, the method may provide for monitoring a physiological response of a patient to a change in the patient's temperature, step 104. More particularly, the monitoring may include the step of selective interconnection of a non-invasive monitoring device to a patient. In one approach, one or more interconnectable/disconnectable monitoring device(s) may be fixedly positioned to a patient to measure patient motion. For example, patient shivering response may be monitored, via attachment of an accelerometer to a patient's jaw (e.g. masseter region) and/or via attachment of an accelerometer to a patient's chest (e.g. pectoral region) and/or via attachment of an accelerometer to a patient's arm (e.g. bicep region) and/or via attachment of an accelerometer to a patient's leg (e.g. quadricep region), wherein one or a plurality of accelerometers are utilized to provide one or a corresponding plurality of accelerometer output signal(s) employable to assess the magnitude and/or stage of shivering and provide an output indication of at least one measure of the of the patient shivering response to cooling.

In other approaches that correlate shivering to a monitored parameter, a blood flow monitoring device may be attached to a patient to measure a degree of vasoconstriction reflective of a degree of shivering (e.g. by measuring relative blood flow at a fingertip and at a corresponding forearm location). In an additional approach, the monitoring device may comprise one or more electromyography (EMG) surface sensors for monitoring muscular electrical activity. In yet a further approach, the monitoring device may comprise one or more capnography input sensors for concentration and/or partial pressure of carbon dioxide in patient respiratory gases. In yet another correlative approach, a pulse oximeter sensor may be interconnected to a patient to measure a patient's blood oxygen saturation level, wherein such level may be correlated to a degree of shivering.

With further reference to FIG. 2, the method may provide for the generation of an output based upon, at least in part, a monitored patient temperature response, step 106. By way of example, such output generation may entail the provision of a visual or auditory output. In one embodiment the method may further include processing of a monitoring signal in accordance with the selected one of a plurality of treatment protocols comprising corresponding preset data/algorithms. In one approach, use of a given protocol may provide for user selection of a given anti-shivering medicament or combination(s) thereof, as well as a corresponding output of information relating to dosage and/or frequency information for the selected medicament(s).

Pursuant to the generation of an output based upon a monitored patient response, the method may encompass use of the output to control a patient shivering response, step 108. For example, information regarding dosage and/or frequency of a given anti-shivering medicament may be employed by a user in conjunction with the actual administration of the medicament.

As illustrated by FIG. 2, the steps of monitoring 104, generating 106 and/or using 108 may be repeated on an ongoing basis during a given thermotherapy procedure, wherein as part of the monitoring step, the patient's response to prior actions taken to control shivering may be assessed (e.g. via trend data assessment) and the output provided in step 108 may take into account the results of such assessment.

As further illustrated in FIG. 2, output may be provided in relation to the generation step 106 that may be utilized in conjunction with controlling a degree of cooling provided by a cooling system, step 110. By way of example, in the generating step 106 an input signal may be provided to a cooling system. Such input signal may be utilized by the cooling system to increase, decrease or maintain a rate of patient cooling.

Figure 4:
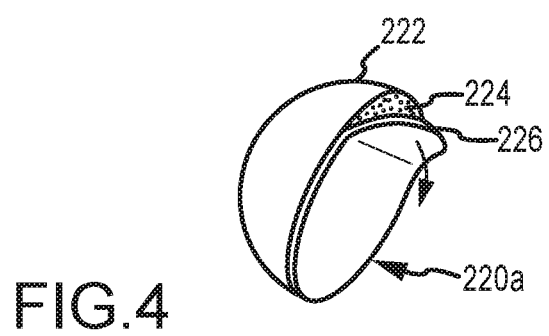
FIG. 4 illustrates one embodiment of a monitoring device employable in the system embodiment of FIG. 3.
Figure 5:
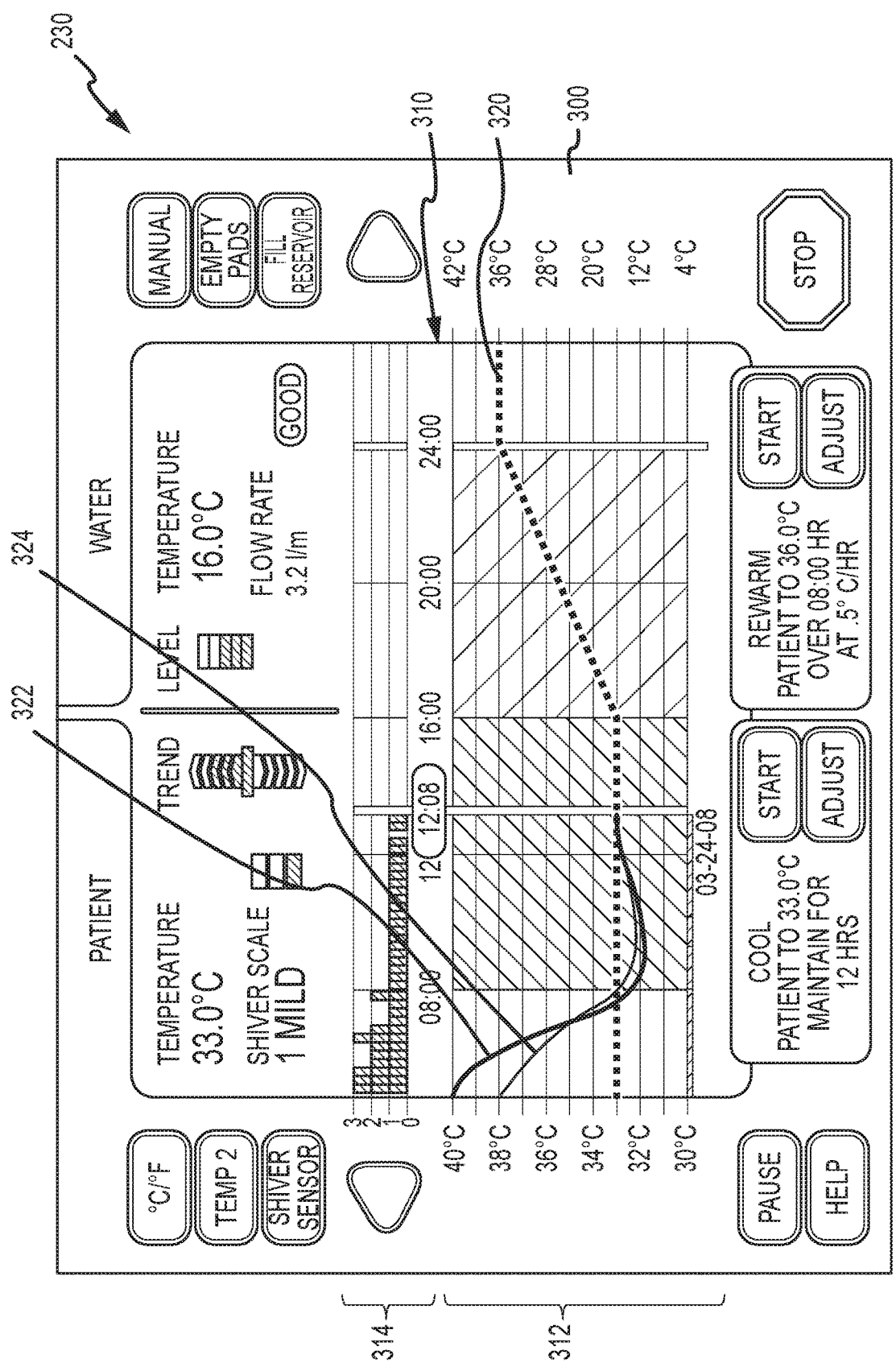
FIG. 5 illustrates one embodiment of an output device employable in conjunction with implementations of the present invention.

Referring now to FIGS. 4 and 5, a further embodiment of the present invention will be described. As shown, a patient P may be cooled utilizing a cooling system comprising contact pads 200 and a control unit 202 that circulates cooled fluid via supply line(s) 204 and return line(s) 206 though the contact pads 200 (e.g. under negative pressure). In this embodiment, the control unit 202 may further comprise a transceiver 210 for transmitting/receiving wireless signals to/from a motion sensor monitoring device 220a interconnected to the chin of a patient P.

By way of example, and with reference to FIG. 4, the motion sensor 220a may include an accelerometer housed within a housing 222 having an adhesive backing 224 and removable liner 226 initially provided therewith. To initiate patient use, the liner 226 may be selectively removed, wherein the adhesive backing 224 may be mounted to a jaw of a patient. In one approach, an on-board battery may be housed in housing 222, e.g. for powering the accelerometer and an on-board transmitter for transmitting a monitoring signal 214 indicative of a magnitude of motion of the patient's chin.

In another approach, the transceiver 210 provided with the control unit 202 may be adapted to transmit a query/power signal 212 to the motion sensor 220a. In turn, the motion sensor 220a may transmit a monitoring signal 214 to the transceiver 210 which is indicative of a degree of motion of the patient's chin. More particularly, the motion sensor 220a may comprise a transreceiver and rectifier arrangement for receiving a query/power signal 212, transducing electrical energy therefrom, and using the energy to generate and transmit the monitoring signal 214.

As may be appreciated, a plurality of motion sensors 220 may be employed. For example, motion sensors 220b and 220c, of like configuration to motion sensor 220a, may be selectively interconnected to different body regions (e.g. an arm and leg of a patient). In such an arrangement, each of the sensors 220a, 220b and 220c may provide a wireless monitoring signal 214.

The monitoring signal(s) 214 may be processed at the control unit 202 in accordance with the described functionalities to provide an output (e.g. a visual or auditory output) at a user interface 230. As previously noted, the output may provide an indication of a magnitude or stage of patient shivering. Additionally or alternatively, such output may provide anti-shivering medicament related information, e.g. dosage and/or frequency information for use by medical personnel in the administration of an anti-shivering medicament. As further reflected by FIG. 4, control unit 202 may include a user input 240 (e.g. a keyboard, touch-screen or point-and-click interface) for user selection of a given anti-shivering treatment protocol, for inputting instructions and/or data regarding the type, amount and timing of medicament administration, and/or for inputting patient-specific information. In conjunction with control operations, the control unit 202 may be further provided for use in controlling patient cooling in accordance with a pre-established protocol(s), e.g. as taught by U.S. Pat. Nos. 6,620,187, 6,692,518, 6,818,012, and 6,827,728, the entirety of which are hereby incorporated by reference.

Figure 3:
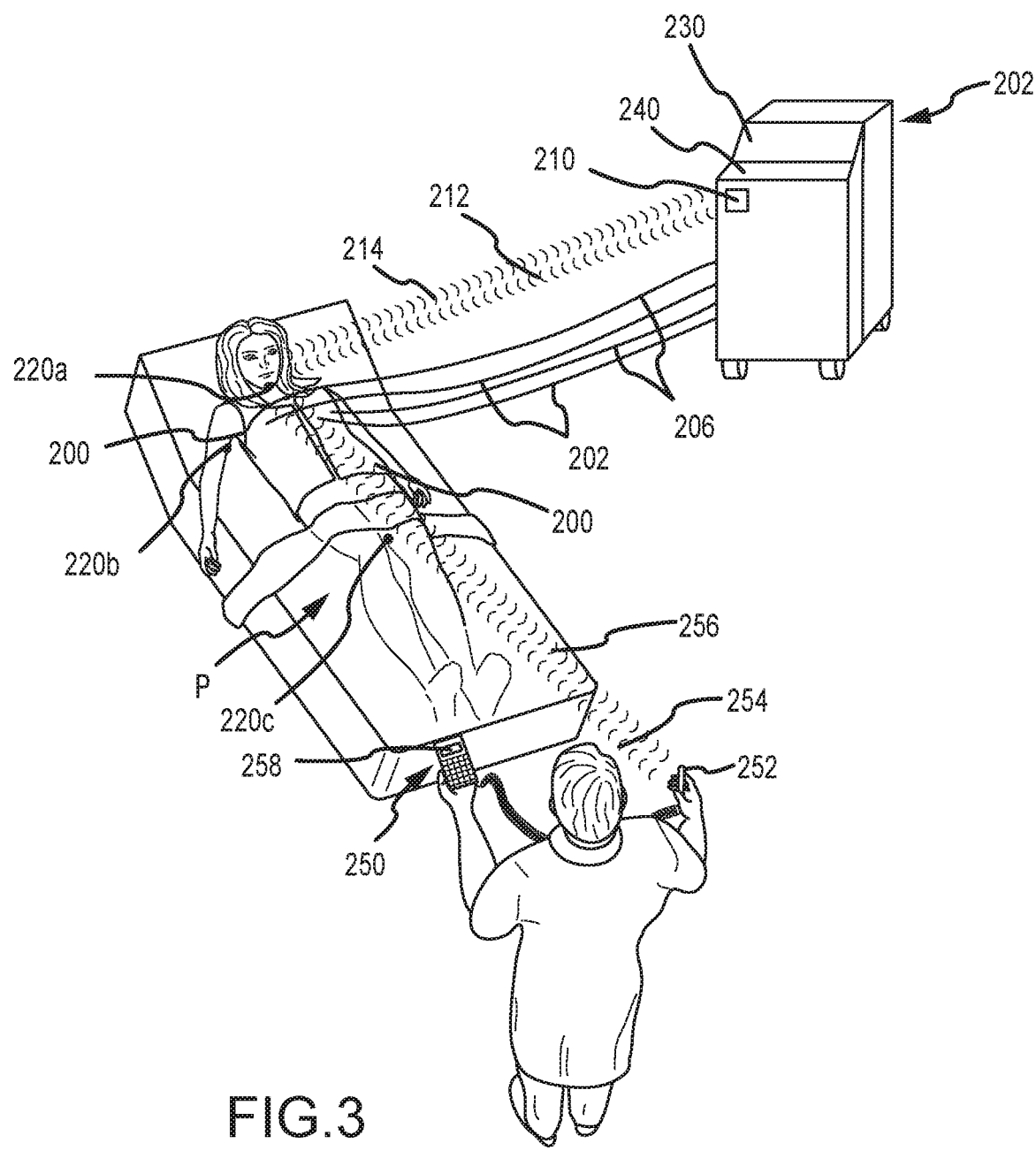
FIG. 3 illustrates a system embodiment comprising the present invention.

As further reflected by FIG. 3, and as an option to control unit 202, a handheld unit 250 may be provided that includes a transceiver 252 for use in transmitting signals 254 and receiving signals 256 to/from the monitoring device 220. As illustrated, the hand held unit may 250 comprise a user output 258 for providing treatment related information.

Figure 6:
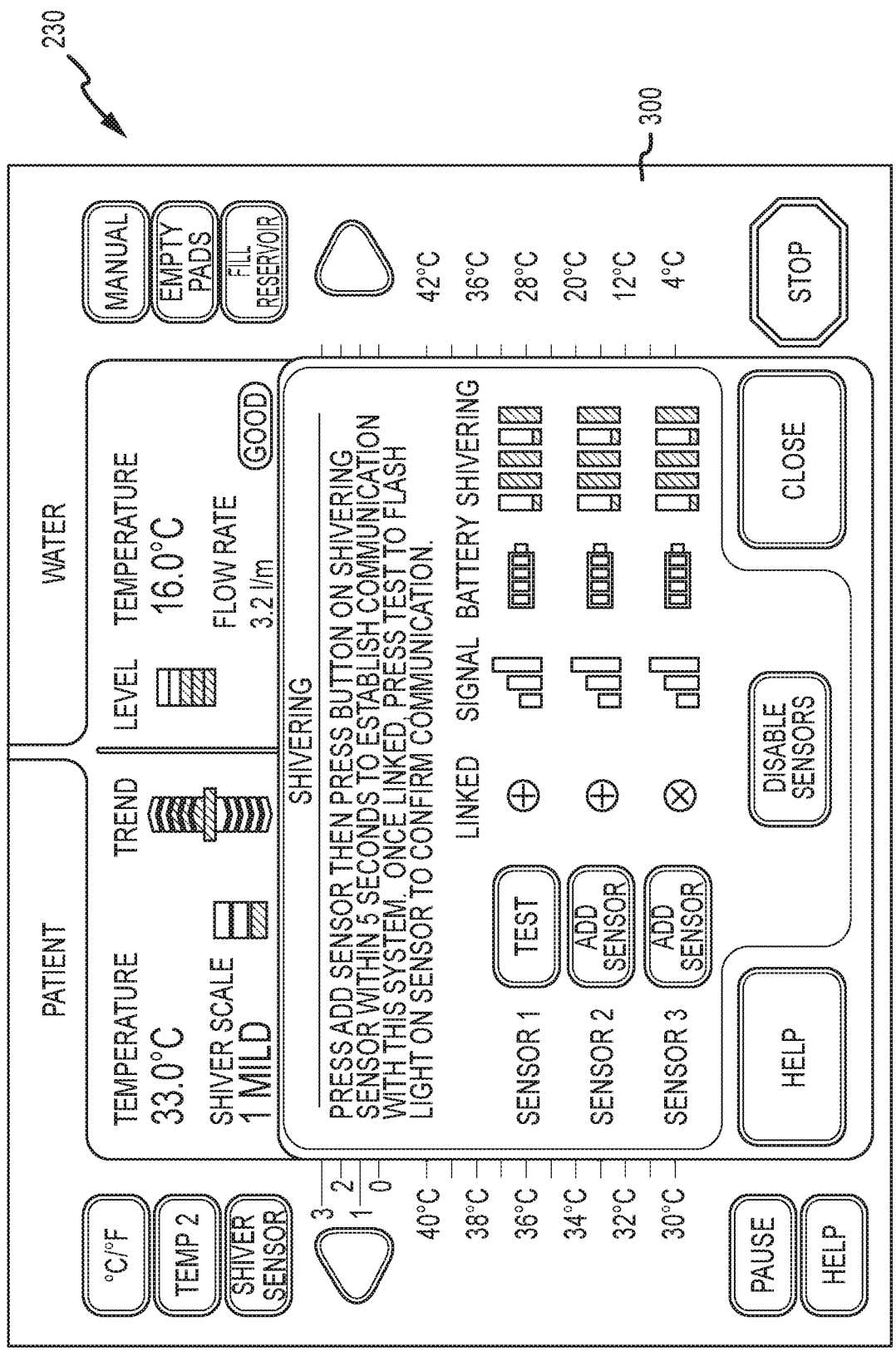
FIG. 6 illustrates the output embodiment device of FIG. 5.

In further relation to the above-described functionality, reference is now made to FIGS. 5 and 6 which illustrate an embodiment of a user interface 230 that may be provided at control unit 202. As illustrated in FIG. 5, the user interface 230 may be provided to allow a user to selectively access various interactive screens for use in conjunction with a given patient therapy in which control unit 202 may be employed to circulate cooled and/or warmed fluid through contact pads 200 to adjust a patient's temperature in accordance with a predetermined and/or otherwise controllable protocol.

As shown in FIG. 5, an interactive screen 300 may be provided at user interface 230 which includes a graphic display portion 310 that graphically illustrates temperature-related data in a first region 312 as a function of time, and that further illustrates patient motion data, e.g. shivering data, as a function of time in a second region 314. The first region 312 may present a first plot 320 of a target patient temperature level as a function of time, e.g. a predetermined patient temperature adjustment rate plot reflecting a desired patient temperature to be reached by controlling the temperature of the circulated fluid. Further, a second plot 322 of a measured patient temperature as a function of time may be presented. Additionally, a third plot 324 of a measured temperature of the fluid circulated by control unit 202 though contact pads 200 may be provided.

In relation to the target patient temperature plot 320, the control unit 202 may include an on-board processor pre-programmed or otherwise programmable to facilitate automated control over patient temperature adjustment therapy. In the later regard, the control unit 202 may be provided with a pre-programmed control module to facilitate automated control over the temperature of the circulated fluid so as to cool a patient in accordance with programmable protocol data during a first phase of treatment, and to re-warm a patient in accordance with another programmable protocol during a second phase of treatment.

As shown by FIG. 5, the second region 314 of the screen 300 may be provided to visually display patient motion data in relation to a predetermined magnitude scale. By way of example, a plurality of predetermined levels of patient motion, or degrees of shivering, may be graphically presented as a function of time. In the illustrated example, four levels of detected patient motion may be provided to a user, wherein no visual indication is provided for a low, or "zero" level of motion, and wherein increasing level of motions may be graphically presented by one, two or three stacked "box" indicators.

As may be appreciated, by visually monitoring the magnitude of shivering response displayed in the second region 314 of the screen 300, medical personnel may assess the need and/or desirability for taking responsive action. For example, such responsive action may include the administration of anti-shivering medicaments and/or the application of surface warming therapy to selected patient body regions and/or a modification to the patient cooling/warming protocol discussed hereinabove (e.g. decreasing a target patient cooling rate and/or a increasing targeted temperature for patient cooling).

As reflected by FIG. 6, screen 300 may also be employable in conjunction with the operation of one or a plurality of motion sensors employable to provide a monitoring signal. By way of example, such motion sensors may be in the form of motion sensors 220a, 220b and 220c discussed hereinabove in relation to FIG. 3. As shown in FIG. 6, interactive screen 300 may be provided to visually facilitate the establishment of wireless communications with each of the sensors, to visually indicate the communication signal strength for each of the motion sensors 220a, 220b and 220c, to visually indicate a battery power level at each of the motion sensors 220a, 220b and 220c (e.g. as reflected by a portion of corresponding wireless monitoring signals), and/or to visually indicate a detected shivering magnitude corresponding with each of the sensors 220a, 220b and 220c.

Figure 7A:
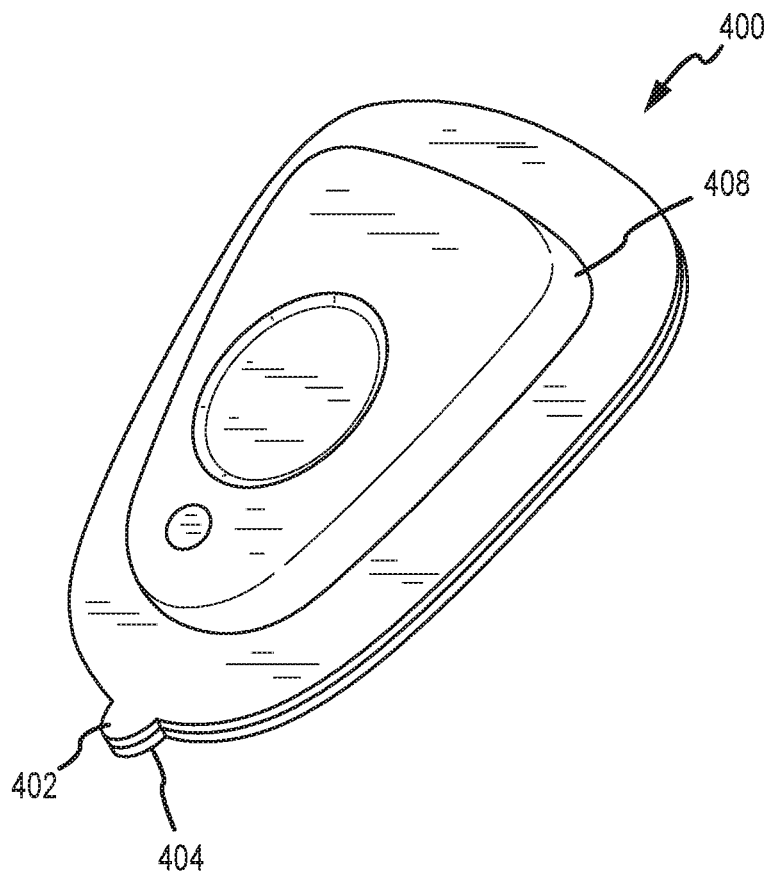
FIGS. 7A, 7B and 7C illustrate perspective views of a motion sensor embodiment and component parts thereof employable to generate a monitoring signal in conjunction with implementations of the present invention.
Figure 7B:
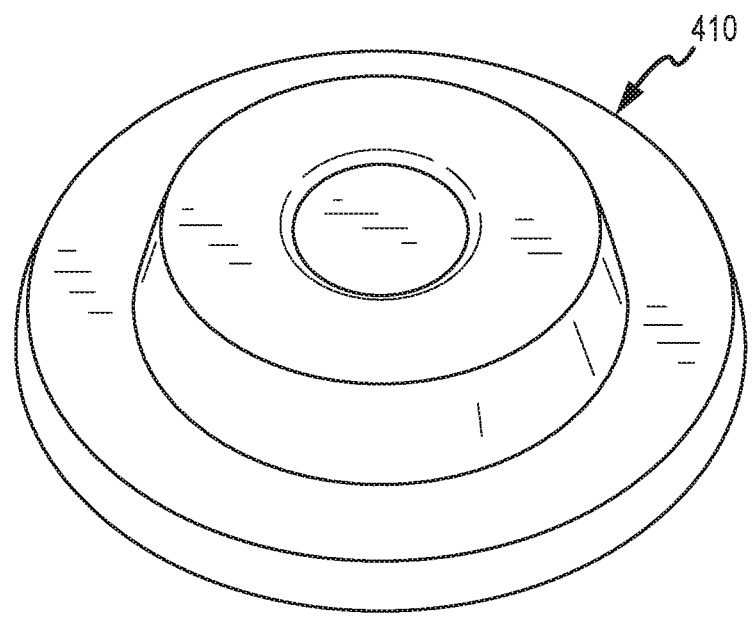
Figure 7C:
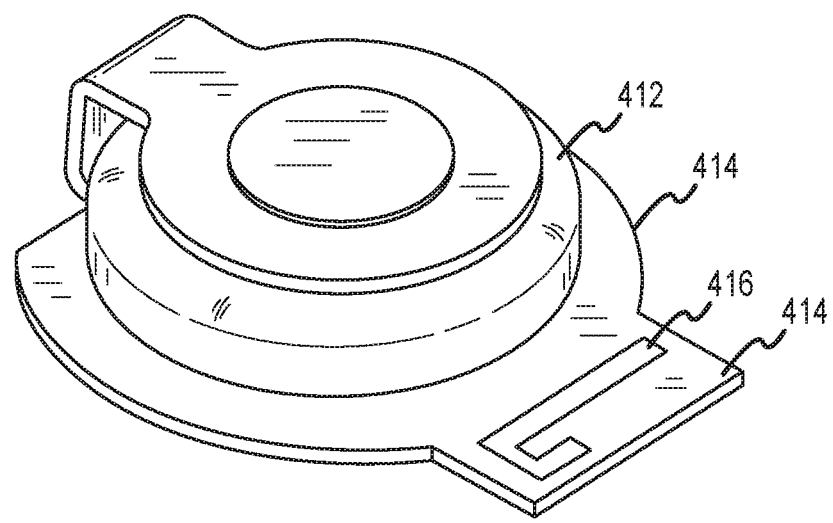

Reference is now made to FIGS. 7A, 7B and 7C illustrating another embodiment of a motion sensor 400. As shown in FIG. 7A, the sensor 400 may include a base pad 402 initially provided with a removable liner 404 overlaying an adhesive bottom surface of the base pad 402. As may be appreciated, the liner 404 may be selectively removed prior to adhesive interconnection of the motion sensor 400 to a patient. The motion sensor 400 further includes a housing portion 408 that houses a sealed sensor assembly 410 which is shown in FIG. 7B. As illustrated in FIG. 7C, of the sensor assembly 410 may include an accelerometer module 412 that is located between opposing circuit elements mounted on opposing, inside surface(s) of a wrap-around circuit board 414. In the illustrated embodiment, a transceiver device 416, e.g. an RF antenna, may be patterned on a stub portion 418 of the circuit board 414 for wireless transception of monitoring signals and power signals. In the later regard, circuit correspondingly located on circuit board 414 may include a rectifier and/or battery for powering the sensor operations. In other embodiments, the patterned antenna 416 may be replaced by a chip transceiver mounted on the circuit board 414.

Figure 8A:
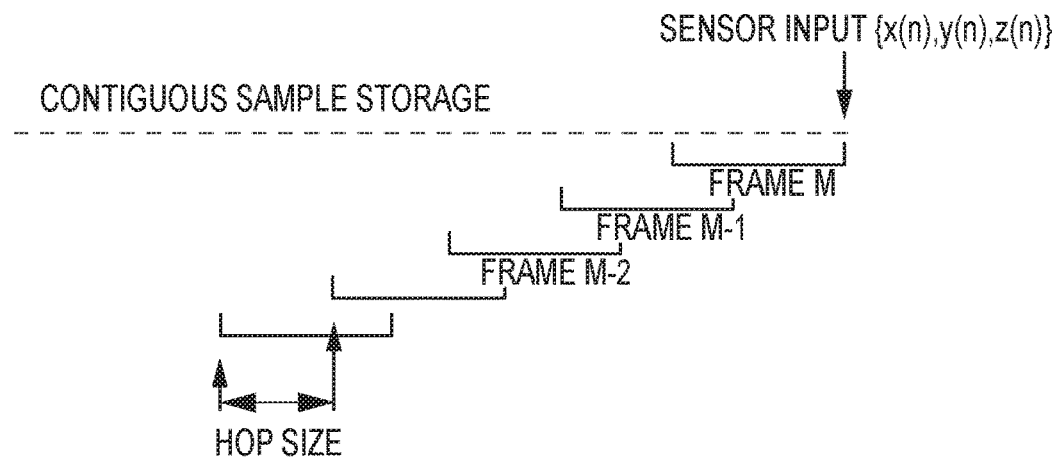
FIGS. 8A, 8B, 8C and 8D illustrate steps corresponding with a frequency domain processing embodiment for processing a monitoring signal in one embodiment of the present invention.
Figure 8B:
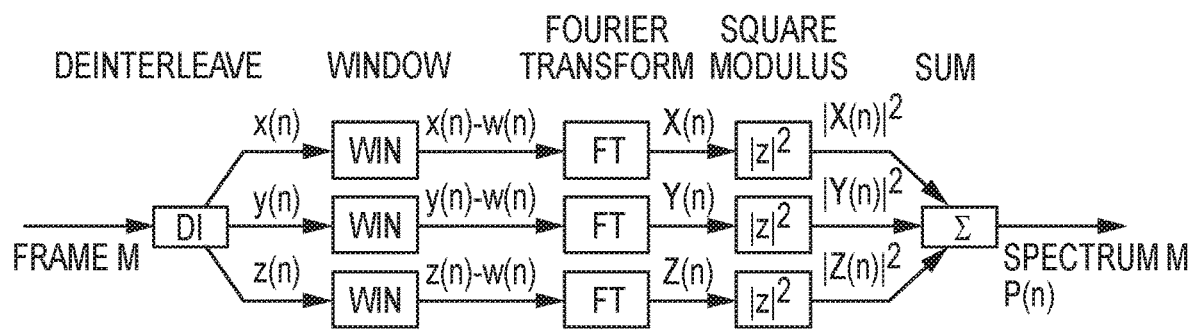
Figure 8C:
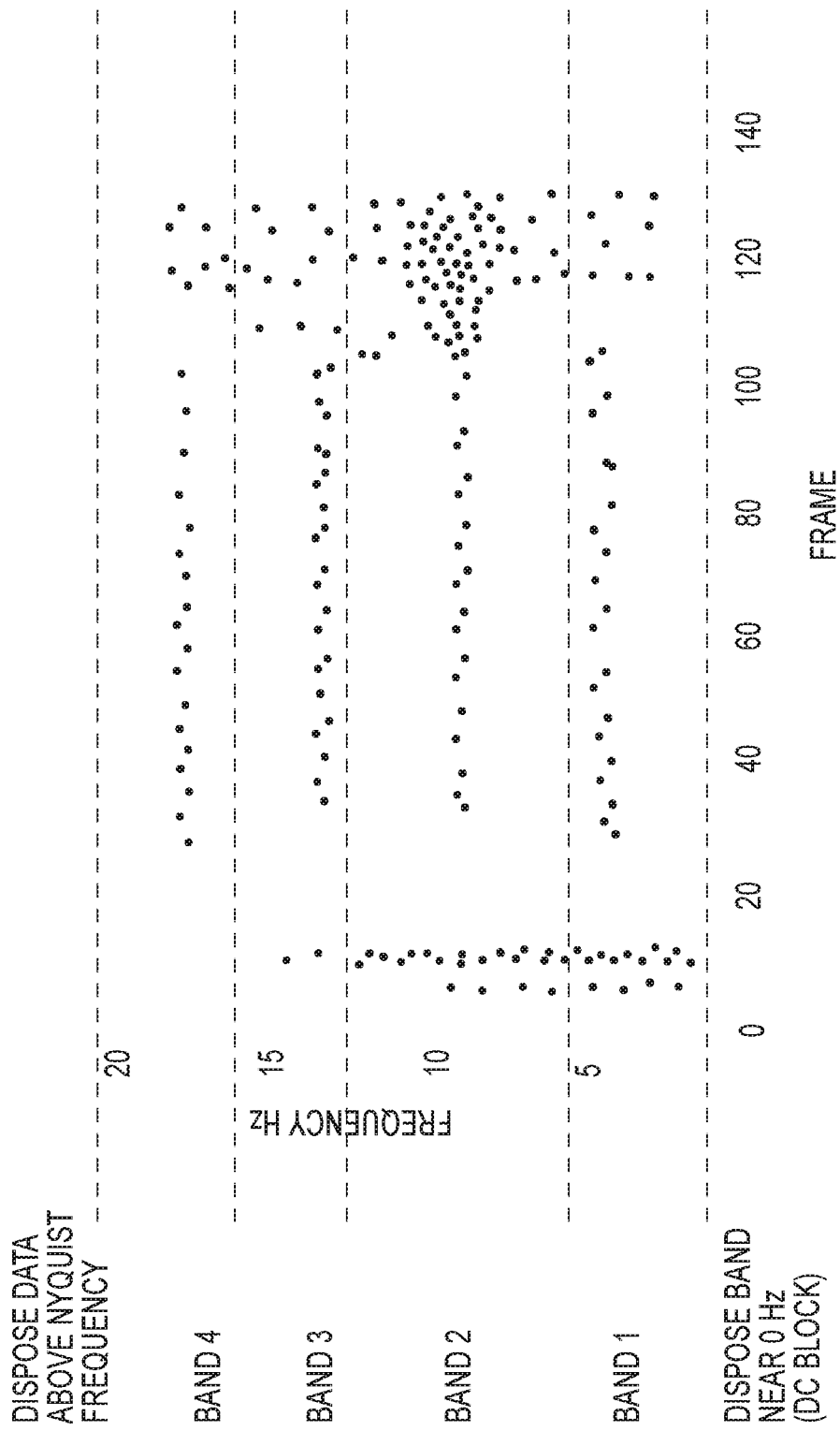

Referring again now to FIG. 1, and as noted above, a processor or logic circuit 20 may be provided to utilize one or a plurality of monitoring signal(s) 12 provided by one or a plurality of monitoring device(s) 10 to yield an output 22. In that regard, and by way of example, a processor 20 may be preprogrammed for time domain and/or frequency domain processing of a monitoring signal provided by a monitoring device 10 that includes a three-dimensional accelerometer as a motion sensor, and for providing a monitoring signal indicative of acceleration in each of three-dimensions as a function of time. In this regard, it may be desirable for the accelerometer to sample at about twice the highest frequency component of interest (e.g. at least about 40 Hz). Reference is now made to FIGS. 8A-8C which illustrate a frequency domain processing embodiment.

As shown in FIG. 8A, a monitoring signal 12 may be provided as a sensor input comprising a stream of sequential data sample sets, wherein each data set comprises data corresponding with a measured magnitude related to acceleration in each of the three dimensions, x, y and z, (e.g. a measured voltage magnitude for each of three-dimensions). In turn, overlapping frames of data sets may be processed, wherein each frame m comprises a plurality of data sets n and wherein sequential ones of such frames at least partially overlap and are at least partially different, (e.g. the "hop" reference in FIG. 8A). In one embodiment, each frame may comprise about 512 data sets.

As shown in FIG. 8B, for each frame m of n data sets, the corresponding data sets may be deinterleaved to yield three data portions corresponding with each of the three dimensions, e.g. x(n), y(n) and z(n). Then, the three data portions may be windowed, e.g. utilizing a Kaiser windowing approach. The windowed data may be further processed according to a Fourier transform function to obtain frequency domain data. In turn, a square of the modulus of the frequency domain data may be determined for each of the three-dimensional data sets corresponding with a given frame, and the resultant values may summed to generate a spectral output for each frame. In turn, the spectral output for a plurality of frames of data may be analyzed on an ongoing basis to detect and assess patient motion.

In this regard, reference is now made to FIG. 8C which illustrates exemplary spectral data corresponding with multiple frames of data (e.g. about 130 frames). In particular, for each frame of data a corresponding spectral distribution across a predetermined frequency range of about 0 Hz to about 20 Hz is shown, wherein the magnitude corresponding with a given frequency is reflected by the number or concentration of data points. In relation to the illustrated example, the spectral data may be analyzed in relation to a plurality of frequency bands, e.g. a first band of about 0 Hz to 5.5 Hz, a second band of about 5.5 Hz to 12.5 Hz, a third band of about 12.5 Hz to 16 Hz, and optionally a fourth band of about 16 Hz to 20 Hz.

Of particular interest is the spectral data corresponding with the second frequency band of about 5.5 Hz to about 12.5 Hz. In this regard, it has been recognized that shivering is most frequently reflected by a patient motion component that is centered at about 9.5 Hz. In the example of FIG. 8C, for the second frequency band, it may be seen that patient shivering may be indicated in relation to the spectral data corresponding with data frames beginning at about frame "40", wherein increasing degrees of shivering are reflected from about frame "110" to frame "120". Non-shivering motion may be reflected by the spectral data corresponding with the data frames preceding frame "40".

Figure 8D:
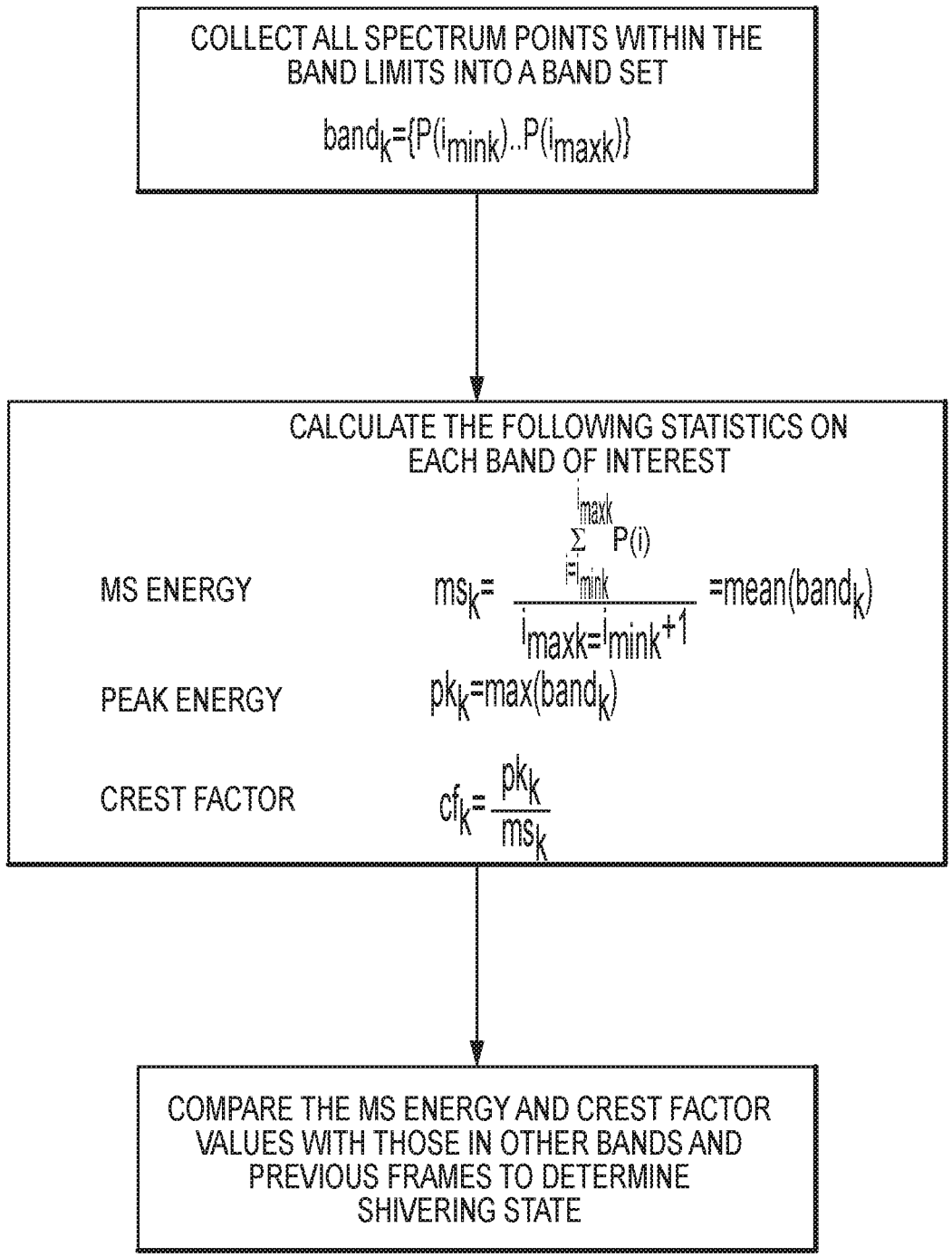

As may be appreciated from the example shown in FIG. 8C, spectral data corresponding with a plurality of successive data frames may be statistically analyzed and processed on an ongoing basis in relation to each of a plurality frequency of bands. In particular, and with reference to FIG. 8C, for a given frame or set of frames, the spectral data points within each frequency band may be collected into a corresponding data set. In turn, for each of the data sets corresponding with each frequency band, a mean square energy value, a peak energy value and a crest factor value may be determined, as shown in FIG. 8D. Thereafter, the mean square energy values, peak energy values, crest factor values for each of the frequency bands may be compared to one another and/or with corresponding values in previous frame sets to detect a predetermined magnitude or degree of motion corresponding with patient shivering.

By way of example, in one approach the mean square energy values and crest factor values for two or more frequency bands may be compared (e.g. a "low" frequency band of about 0 Hz to 5.5 Hz, a "middle" frequency band of about 5.5 Hz to 12.5 Hz, and an "upper" frequency band of about 12.5 Hz to 16 Hz), wherein a calculated mean square energy value of the lower band which is greater than or equal to a calculated mean square energy value for the upper band, together with a crest factor value for all three bands that is less than a predetermined value (e.g. a relatively low value), may indicate the absence of or a relatively low level of patient motion. Further, a rise in the mean square energy value and crest factor value for each of the bands may indicate patient motion. And, a rise in the mean square energy value for the middle band (e.g. encompassing the 9.5 Hz level typically related to shivering) relative to the low and high bands, together with a decrease in the crest factor value for the middle band, may indicate the presence and/or a degree of patient shivering.

Figure 9A:
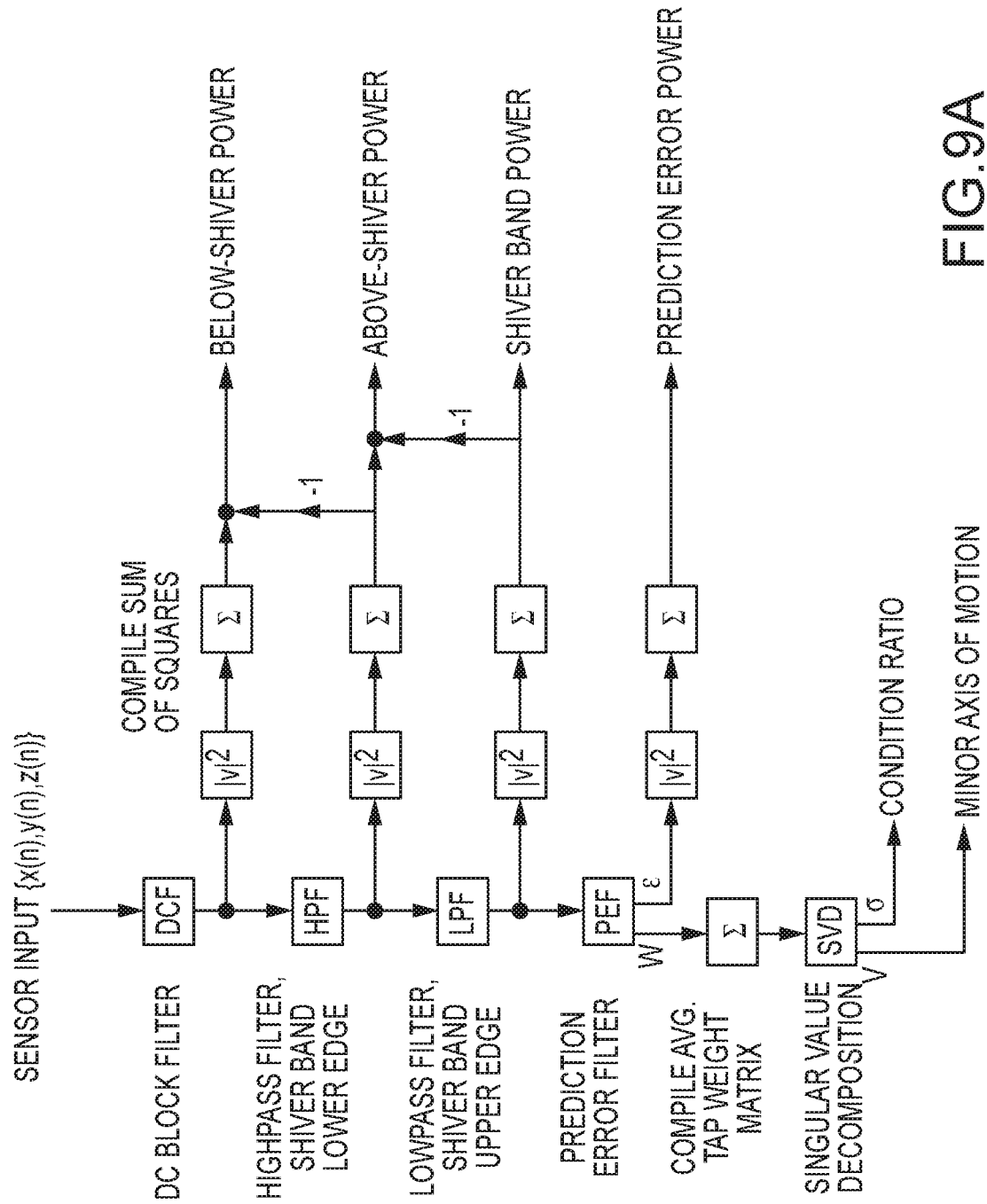
Figure 9B:
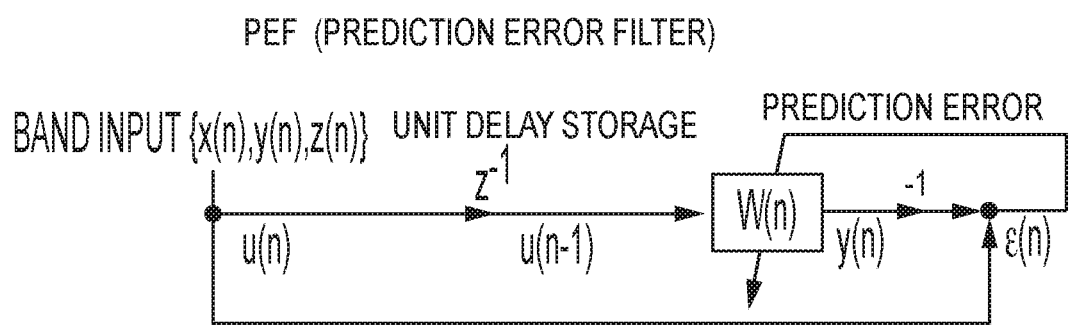

As noted above, a monitoring signal 12 may also be processed via time domain processing. In one embodiment shown in FIGS. 9A-9C, a monitoring signal, or sensor input, three-dimensional accelerometer output data may be filtered and processed to yield power values associated with a predetermined plurality of frequency bands. In turn, the power values may be analyzed to obtain an indication of a magnitude degree and/or stage of shivering. By way of example, and as shown in FIG. 9A, the monitoring signal may comprise sets of three-dimensional data that may be filtered to block, or remove, DC frequency components (e.g. to reduce or remove gravitational influences). In turn, a square of a modulus value corresponding with the three-dimensional data sets may be computed and summed for each and/or a plurality of frames of data sets. Such processing may be conducted without frequency filtering to obtain a first power value. Further, such processing may be conducted after applying a high-pass filter (e.g. to filter out or remove frequency components in a lower band (of about 5.5 Hz or less)) to obtain a second power value, and after applying both a high-pass filter and a low-pass filter (e.g. filter out or remove frequency components above about 12.5 Hz) to obtain a third power value. The second and third power values may be subtracted from the first power value to obtain a power value associated with a lower, or "below-shiver", frequency band (e.g. about 0 Hz to 5.5 Hz). Further, the third power value may be subtracted from the second value to obtain a power value associated with a higher, or "above-shiver", frequency band (e.g. above about 12.5 Hz). Finally, the third power value may be understood to be associated with a middle frequency band, or "shiver band", (e.g. about 5.5 Hz to 12.5 Hz).

As further reflected by FIG. 9A after high-pass and low-pass filtering of the monitoring signal, the filtered data sets may be further processed via a prediction error filter (PEF) to yield a prediction error power value. In this regard, an adaptive filter (e.g. a first-order least mean squares adaptive filter) may be applied, as reflected by FIG. 9B. Further, an output of the predictive error filter may be employed in conjunction with a single value decomposition (SID) spatial analysis to obtain a condition ratio value and minor axis of motion value, as reflected by FIG. 9B.

In turn, the above-noted values may be utilized to assess shivering. For example, in one approach the below-shiver band, above-shiver band and shiver-band power values may be compared, wherein a below-shiver band power value that is greater than or equal to that of the other bands, together with a condition ratio that is less than a predetermined value (e.g. a relatively low value), may indicate the absence of or a relatively low level of patient motion. Further, a rise in the shiver-band power value, a rise in the condition ratio, and a rise in a shiver-band power value-to-prediction error power value ratio, (e.g. shiver-band power value/prediction error power valve) may combinatively indicate patient motion. Further, a rise in the shiver-band power value, coupled with a decrease in the condition ratio and a decrease in the shiver-band power value-to-prediction error power value ratio, may indicate the presence and/or a degree of patient shivering.

Additional embodiments to those described above will be apparent. For example, in relation to the motion sensor 400 of FIG. 7A-7C, the sensor 400 may be modified to include one or more output devices for providing an output at sensor 400 indicative of a detected magnitude or level of detected patient shivering, e.g. one or more LED (i.e. light emitting diode) interconnected to the sensor 400 for co-movement therewith (e.g. wherein illumination of an LED indicates detected shivering above a predetermined level and/or wherein illumination of different ones or sets of a plurality of LED's may be employed to indicate corresponding degrees of detected shivering). In turn, an on-board processor for processing the monitoring signal, and an on-board power source (e.g. a battery) and/or an on-board wireless energy receiving device (e.g. an RF signal receiver and rectifier) may be included to power the components.

The embodiment descriptions provided above are for purposes illustration and are not intended to limit the scope of the present invention. Additions and modifications will be apparent to those skilled in the art.

What is claimed is:

1. A system for use in a patient cooling therapy procedure, comprising:
    a monitoring device for monitoring patient shivering and for providing a monitoring signal responsive thereto, wherein the monitoring device includes a motion sensor and is selectively interconnectable in fixed relation to and disconnectable from a patient;
    a control unit configurable to cool and warm a circulated fluid through at least one contact pad for thermal exchange with the patient, including:
    at least one processor programmed to:
    control automatically a temperature of the circulated fluid so as to cool and warm the patient in different treatment phases in accordance with a predetermined protocol; and,
    process said monitoring signal to provide an output signal indicative of a magnitude of patient shivering; and,
    a user interface to graphically display, on an ongoing basis as a function of time during the patient cooling therapy procedure, each of the following:
    patient motion data, responsive to said output signal, indicating the magnitude of patient shivering as a function of time, wherein said patient motion data is displayed in relation to a predetermined magnitude scale having a plurality of predetermined levels of patient motion indicative of increasing degrees of patient shivering a predetermined patient temperature adjustment rate plot indicating a desired patient temperature to be reached as a function of time;
    a measured patient temperature plot indicating a measured patient temperature as a function of time; and,
    a measured circulated fluid temperature plot indicating a measured temperature of said circulated fluid as a function of time.

2. A system as recited in claim 1, wherein said user interface provides a screen that includes:
    a graphic display portion that graphically displays said predetermined patient temperature adjustment rate plot, said measured patient temperature plot, and said measured circulated fluid temperature plot in a first region of the graphic display portion, relative to a temperature scale and a time scale.

3. A system as recited in claim 2, wherein said graphic display portion graphically displays said patient motion data in a second region of the graphic display portion, relative to said time scale.

4. A system as recited in claim 1, further comprising:
    at least one of a battery and a wireless energy conversion device, interconnected to said monitoring device for direct co-movement therewith, for powering said monitoring device free from hardwire interconnection with a power source.

5. A system as recited in claim 4, wherein said at least one of battery and wireless energy conversion device being one of directly connected to said monitoring device and interconnected to a common support member together with said monitoring device for co-movement therewith.

6. A system as recited in claim 4, further comprising:
    a transmitter for transmission of a wireless signal corresponding with said monitoring signal, wherein said transmitter comprises an antenna and is interconnected to said monitoring device for co-movement therewith.

7. A system as recited in claim 1, wherein said at least one processor is operable to employ said monitoring signal to generate an input for use in controlling the temperature of the circulated fluid.

8. A system as recited in claim 1, wherein said monitoring device comprises a motion sensor including:
    a three-dimensional accelerometer, wherein said monitoring signal comprises three-dimensional acceleration data and comprises a stream of sequential data sets.

9. A system as recited in claim 8, wherein said at least one processor is programmed to:
    process said monitoring signal utilizing frequency domain processing to provide said output signal, wherein in said process said at least one processor is programmed to process a plurality of frames of said sequential data sets on an ongoing basis to determine spectral data corresponding with each different one of said plurality of frames of said sequential data sets, wherein each frame of said plurality of frames of said sequential data sets comprises a plurality of said sequential data sets, wherein sequential ones of said plurality of said frames of said sequential data sets are partially overlapping and partially non-overlapping, and wherein for said plurality of frames of said sequential data sets the at least one processor is programmed to collect and analyze spectral data sets corresponding with each different one of a plurality of different, predetermined frequency bands to detect said magnitude of patient shivering.

10. A system as recited in claim 9, wherein each of said sequential data sets comprises data corresponding with a measured magnitude related to acceleration in each of said three dimensions.

11. A system as recited in claim 10, wherein for each frame of said plurality of frames said at least one processor is programmed to:
   de-interleave said frame to obtain three data portions corresponding with each of said three dimensions;
   window said three data portions; and,
   transform the three windowed data portions to obtain three corresponding frequency domain data portions.

12. A system as recited in claim 11, wherein for each frame of said plurality of frames said at least one processor is programmed to:
   utilize the three corresponding frequency domain data portions to obtain a corresponding spectral output.

13. A system as recited in claim 9, wherein said plurality of different, predetermined frequency bands includes at least a predetermined first frequency band and a different, predetermined second frequency band, wherein only one of said predetermined first frequency band and said predetermined second frequency band includes a frequency of 9.5 Hz.

14. A system as recited in claim 9, wherein said plurality of different, predetermined frequency bands includes at least three non-overlapping frequency bands, only one of which includes a frequency of 9.5 Hz.

15. A system as recited in claim 9, wherein for each frame of said plurality of frames the at least one processor is programmed to:
   analyze the spectral data sets corresponding with each of said plurality of different, predetermined frequency bands to determine a mean square energy value, a peak energy value and a crest factor; and,
   compare the mean square energy values, peak energy values, and crest factor values for each of the plurality of different, predetermined frequency bands to one another or with previously determined, corresponding values to detect a degree of motion corresponding with patient shivering.

* * * * *